United States Patent [19]

Hammond et al.

[11] 4,354,950
[45] Oct. 19, 1982

[54] MANNICH BASE DERIVATIVE OF HYDROXYARYL SUCCINIMIDE AND HYDROCARBON OIL COMPOSITION CONTAINING SAME

[75] Inventors: Kenneth G. Hammond, Poughkeepsie; Garren E. Maas, Wappinger Falls, both of N.Y.

[73] Assignee: Texaco Inc., White Plains, N.Y.

[21] Appl. No.: 221,071

[22] Filed: Dec. 29, 1980

[51] Int. Cl.$^3$ .............................................. C10M 1/32
[52] U.S. Cl. ...................... 252/51.5 A; 260/326.5 FM
[58] Field of Search ...................... 252/51.5 A, 51.5 R; 260/326.5 FM

[56] References Cited

U.S. PATENT DOCUMENTS

| | | | |
|---|---|---|---|
| 3,219,666 | 11/1965 | Norman et al. | 252/51.5 A X |
| 3,442,808 | 5/1969 | Traise et al. | 252/51.5 A X |
| 3,459,661 | 8/1969 | Schlobohm | 252/51.5 A X |
| 4,248,725 | 2/1981 | Crawford et al. | 252/51.5 A |
| 4,285,824 | 8/1981 | Bryant | 260/326.5 FM X |

FOREIGN PATENT DOCUMENTS

| | | | |
|---|---|---|---|
| 825212 | 10/1969 | Canada | 252/51.5 A |
| 51-8304 | 1/1976 | Japan | 252/51.5 A |
| 1194286 | 6/1970 | United Kingdom | 252/51.5 A |
| 2017108A | 10/1979 | United Kingdom | 252/51.5 A |

Primary Examiner—Andrew Metz
Attorney, Agent, or Firm—Carl G. Ries; Robert A. Kulason; James J. O'Loughlin

[57] ABSTRACT

A Mannich base derivative of a hydroxyaryl succinimide represented by the formula:

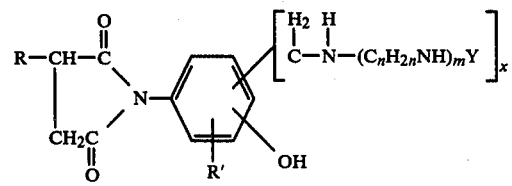

in which R is a hydrocarbyl radical having from about 25 to 200 carbon atoms, R' is hydrogen, an alkyl radical or a halogen radical, n has a value of 2 or 3, m has a value from 1 to 5, Y is hydrogen or a methylene hydroxyaryl succinimide radical, and x has a value of 1 to 2 when Y is hydrogen and a value of 1 when Y is a methylene hydroxyaryl succinimide radical is provided, as well as a method of preparation and a hydrocarbon lubricating oil composition containing same.

13 Claims, No Drawings

MANNICH BASE DERIVATIVE OF HYDROXYARYL SUCCINIMIDE AND HYDROCARBON OIL COMPOSITION CONTAINING SAME

BACKGROUND OF THE INVENTION

Field of the Invention

Internal combustion engines operate under a wide range of temperatures including low-temperature stop-and-go service as well as high temperature conditions produced by continuous high speed driving. Stop-and-go driving, particularly during cold, damp weather conditions, leads to the formation of sludge in the crankcase and oil passages of a gasoline engine. This sludge seriously limits the ability of the crankcase oil to lubricate the engine. In addition, the sludge tends to contribute to rust formation within the engine. The noted problems are compounded by lubrication service maintenance recommendations calling for extended oil drain intervals.

It is known to employ nitrogen-containing dispersants and/or detergents in the formulation of crankcase lubricating oil compositions. Many of the known dispersant/detergent compounds are based on the reaction of an alkenylsuccinic acid or anhydride with an amine or polyamine to produce an alkenylsuccinimide or an alkenylsuccinamic acid as determined by selected conditions of reaction.

It is also known to chlorinate alkenylsuccinic acid or anhydride prior to the reaction with an amine or polyamine in order to produce a reaction product in which a portion of the amine or polyamine is attached directly to the alkenyl radical of the alkenylsuccinic acid or anhydride. The thrust of many of these processes is to produce a dispersant having a relatively high level of nitrogen. The noted known processes generally result in the production of a dispersant reaction product typically containing from about 0.5 to 5% nitrogen. These dispersant additives exhibited a high degree of oil solubility and have been found to be effective for dispersing the sludge that is formed under severe low temperature stop-and-go engine operating conditions. However, it has become increasingly difficult to formulate lubricants with these additives which meet the present requirements with respect to the prevention or inhibition of the formation of varnish.

SUMMARY OF THE INVENTION

The Mannich base derivative of N-(hydroxyaryl) hydrocarbyl succinimide of this invention is represented by the formula:

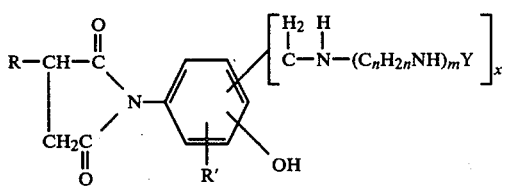

in which R is a hydrocarbyl radical having from about 25 to 200 carbon atoms, R' is hydrogen, an alkyl radical or a halogen radical, n has a value of 2 or 3, m has a value from 1 to 5, Y is hydrogen or a methylene hydroxyaryl succinimide radical, and x has a value of 1 to 2 when Y is hydrogen and a value of 1 when Y is a methylene hydroxyaryl succinimide radical.

The novel Mannich base derivative of this invention is prepared by reacting a hydrocarbyl substituted succinic anhydride with an aminophenol to produce an intermediate N-(hydroxyaryl)hydrocarbyl succinimide. This intermediate is then reacted with an alkylene diamine or polyalkylene polyamine and an aldehyde in a Mannich base reaction to produce the prescribed Mannich base derivative.

The novel lubricant concentrate or lubricating oil composition comprises a base oil of lubricating viscosity and an appropriate amount of the prescribed Mannich base derivative of an N-(hydroxyaryl)hydrocarbyl succinimide.

DESCRIPTION OF THE PREFERRED EMBODIMENT

The novel Mannich base derivative of N-(hydroxyaryl)hydrocarbyl succinimide of this invention is represented by the formula:

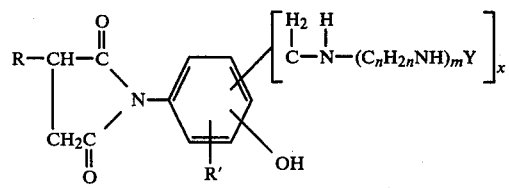

in which R is a hydrocarbyl radical having from about 25 to 200 carbon atoms, R' is hydrogen, an alkyl radical or a halogen radical, n has a value of 2 or 3, m has a value from 1 to 5, Y is hydrogen or a methylene hydroxyaryl succinimide radical, and x has a value of 1 to 2 when Y is hydrogen and a value of 1 when Y is a methylene hydroxyaryl succinimide radical. The methylene hydroxyaryl succinimide radical represented by Y in the generic formula has the structure:

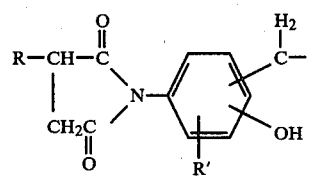

in which R and R' have the values noted hereinabove.

A more preferred additive of the invention is represented by the formula:

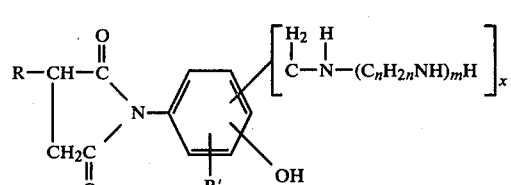

in which R is a hydrocarbyl radical having from about 25 to 200 carbon atoms, R' is hydrogen, an alkyl radical having from 1 to 3 carbon atoms or a halogen radical, n has a value of 2 or 3, m has a value from 1 to 5, and x has a value from 1 to 2.

A still more preferred additive of the invention is a Mannich base derivative of N-(4-hydroxyphenyl) hydrocarbyl succinimide represented by the formula:

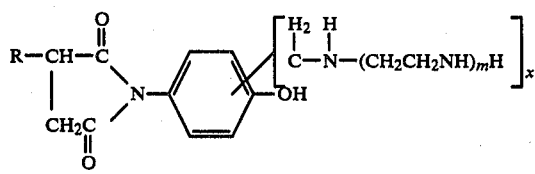

in which R is a hydrocarbyl radical having from about 50 to 100 carbon atoms, m has a value from 1 to 3, and x has a value from 1 to 2.

In instances where greater than the stoichiometric amount of aldehyde is employed in the synthesis, methylene linked oligomers of the aforementioned structures also may be formed.

The prescribed Mannich base derivative of the invention is generally prepared in two steps. In the first step of this reaction a hydrocarbyl succinic anhydride is reacted with an aminophenol to produce an N-(hydroxyaryl) hydrocarbyl succinimide.

The hydrocarbyl succinic anhydride reactant suitable for this reaction is represented by the formula:

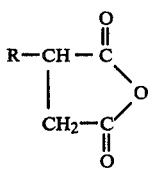

in which R represents a monovalent hydrocarbyl radical having from about 25 to 200 carbon atoms. A preferred starting reactant is one in which the hydrocarbyl radical has from about 50 to 125 carbon atoms. A more preferred reactant is an alkenylsuccinic anhydride in which the alkenyl radical is derived from a relatively high molecular weight olefin or polyolefin and has from about 50 to 100 carbon atoms. Methods for preparing hydrocarbyl succinic anhydrides are well known and do not constitute a part of this invention.

The aminophenol reactant is represented by the formula:

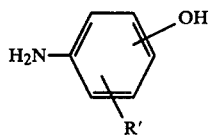

in which R' is hydrogen, an alkyl radical having from 1 to 3 carbon atoms or a halogen radical such as the chloride or bromide radical.

Suitable aminophenols include 2-aminophenol, 3-aminophenol, 4-aminophenol, 4-amino-3-methylphenol, 4-amino-3-chlorophenol, 4-amino-2-bromophenol and 4-amino-3-ethylphenol.

In general, equimolar amounts of the hydrocarbyl substituted succinic anhydride and of the aminophenol are dissolved in an inert solvent (i.e. a hydrocarbon solvent such as toluene, xylene, or isooctane) and reacted at a moderately elevated temperature up to the reflux temperature of the solvent used for sufficient time to complete the formation of the intermediate N-(hydroxyphenyl)hydrocarbyl succinimide. Thereafter, the solvent is removed under vacuum at an elevated temperature, generally, at approximately 160° C. (1 mm).

Alternatively, the intermediate is prepared by combining equimolar amounts of the hydrocarbyl substituted succinimide and the aminophenol, and heating the resulting mixture at elevated temperature under a nitrogen purge in the absence of solvent.

The following examples illustrate the preparation of the intermediate or precursor N-(hydroxyphenyl)hydrocarbyl succinimide.

EXAMPLE 1

A mixture containing polyisobutenyl (approximately 1300 MW) succinic anhydride (1935 g, 1.0 mole based on 58.0 sap no), 4-aminophenol (109 g, 1.0 mole) and toluene (500 ml) was stirred at reflux temperature with continuous removal of water for 4 hours and then stripped of volatiles at 160° C. (1 mm) to yield a clear amber product.

% N: Calculated–0.69. Found—0.60.

EXAMPLE 2

A mixture containing polyisobutenyl (approximately 1300 MW) succinic anhydride (967 g, 0.5 mole based on 58.0 sap no), 2-aminophenol (54.4 g, 0.5 mole) and toluene (300 ml) was stirred at reflux temperature with continuous removal of water for 4 hours and then stripped of volatiles at 160° C. (1 mm) to yield a clear amber product.

% N: Calculated—0.69. Found—0.59.

EXAMPLE 3

A mixture containing polyisobutenyl (approximately 920 MW) succinic anhydride (1300 g, 1.0 mole based on 86.3 sap no), 4-aminophenol (109 g, 1.0 mole) and toluene (500 ml) was stirred at reflux temperature with continuous removal of water for 4 hours and then stripped of volatiles at 160° C. (1 mm) to yield a clear amber product.

% N: Calculated—1.0. Found—0.91.

EXAMPLE 4

A mixture containing polyisobutenyl (approximately 1300 MW) succinic anhydride (3044 g, 1.4 mole based on 51.6 sap no) and 4-aminophenol (153 g, 1.4 mole) was stirred at 160° C. for 4 hours. Volatiles were removed under a nitrogen purge.

% N: Calculated—0.65. Found—0.61.

In the second step of the reaction, an N-(hydroxyaryl)hydrocarbyl succinimide is reacted with a diamine or a polyamine together with an aldehyde in the Mannich base reaction. In general, the reactants are admixed and reacted at an elevated temperature until the reaction is complete. This reaction may be conducted in the presence of a solvent and in the presence of a quantity of mineral oil which is an effective solvent for the N-(hydroxyaryl)hydrocarbyl succinimide intermediate and for the finished Mannich base.

The diamines and polyamines which can be employed are represented by the formula:

in which n equals 2 or 3 and m has a value from 1 to 5. Suitable amines include ethylenediamine, 1,3-propanediamine, diethylenetriamine, triethylenetetramine, tetraethylenepentamine, and pentaethylenehexamine.

The specific reactants and reaction conditions employed for preparing the Mannich bases of this invention via the foregoing procedures are given in the following table:

TABLE I

| Ex. No.[3] | Phenol Precursor Ex. No. | Phenol Precursor Amount Gr(mole)[1] | Amine[5] | Amine Amount Gr(mole) | Formaldehyde Amount Gr(mole) | Solvent | Mole Ratio Phenol-Amine-HCHO | Reaction Temp.[4] °C. | Product Analysis %N Found(Calcd)[2] |
|---|---|---|---|---|---|---|---|---|---|
| 5 | 4 | 2950(1.3) | EDA | 172(2.86) | 156.0(5.2) | n-Butanol 1000 ml | 1-2.2-4 | 100 | 1.3(1.3) |
| 6 | 4 | 226(0.10) | EDA | 12(0.20) | 24.3(0.30) | None | 1-2-3 | 90 | 1.2(1.3) |
| 7 | 4 | 113(0.05) | EDA | 3.0(0.05) | 3.0(0.10) | " | 1-1-2 | 120 | 0.98(0.91) |
| 8 | 4 | 165(0.07) | EDA | 4.2(0.07) | 17.0(0.21) | " | 1-1-3 | 95 | 0.91(0.95) |
| 9 | 1 | 142(0.07) | DETA | 14.4(0.14) | 10.5(0.35) | " | 1-2-5 | 90 | 1.4(1.8) |
| 10 | 1 | 142(0.07) | DETA | 7.2(0.07) | 5.3(0.18) | " | 1-1-2.5 | 90 | 0.9(1.1) |
| 11 | 1 | 142(0.07) | TETA | 20.4(0.14) | 12.6(0.42) | " | 1-2-6 | 90 | 2.0(2.1) |
| 12 | 1 | 404(0.2) | TETA | 58.4(0.4) | 30.0(1.0) | Isopropanol 45 ml | 1-2-5 | 83 | 2.2(2.1) |
| 13 | 4 | 2500(1.1) | TETA | 354(2.4) | 132(4.4) | n-Butanol 800 ml | 1-2.2-4 | 100 | 2.3(2.1) |
| 14 | 4 | 113(0.05) | TETA | 14.6(0.10) | 4.5(0.15) | None | 1-2-3 | 100 | 2.3(2.1) |
| 15 | 1 | 142(0.07) | TETA | 10.4(0.07) | 6.3(0.21) |  | 1-1-3 | 90 | 1.3(1.3) |
| 16 | 2 | 202(0.1) | TETA | 14.6(0.1) | 7.5(0.25) | Isopropanol 45 ml | 1-1-2.5 | 83 | 1.3(1.3) |
| 17 | 3 | 415(0.15) | TETA | 21.6(0.15) | 18.0(0.60) | None | 1-1-4 | 83 | 2.3(2.2) |
| 18 | 4 | 240(0.05) | TETA | 2.6(0.025) | 3.0(0.10) | n-Butanol 50 ml | 1-0.5-2 | 100 | 0.56(0.65) |
| 19 | 1 | 2026(1.0) | TETA | 73.0(0.05) | 82.4(2.5) | Isopropanol 211 ml | 1-0.5-2.5 | 83 | 0.77(0.80) |
| 20 | 4 | 113(0.05) | TEPA | 9.5(0.05) | 3.0(0.10) | None | 1-1-2 | 110 | 1.4(1.6) |
| 21 | 4 | 113(0.05) | TEPA | 18.9(0.10) | 4.5(0.15) | " | 1-2-3 | 110 | 2.6(2.8) |
| 22 | 4 | 113(0.05) | PEHA | 11.6(0.05) | 3.0(0.10) | " | 1-1-2 | 110 | 1.7(1.9) |
| 23 | 4 | 113(0.05) | PEHA | 23.4(0.10) | 4.5(0.15) | " | 1-2-3 | 110 | 2.9(3.2) |

[1]Mole based on sap. no. of original ASAA.
[2]% N calculated from the nitrogen analysis of the N-(hydroxyphenyl)polyisobutenyl succinimide and the nitrogen analysis of the respective amine.
[3]All of the examples were run using Procedure A except Examples 6 and 8 where Procedure B was used.
[4]The reactions were run for 4 hours for Example 7, for 6 hours for Examples 6, 8, 14 and 20 through 23, all of the remainder being run for 8 hours.
[5]EDA = ethylenediamine, DETA = diethylenetriamine, TETA = triethylenetetramine, PEHA = pentaethylenehexamine, TEPA - tetraethylenepentamine.

The aldehyde which can be employed in this reaction is represented by the formula:

RCHO in which R is a hydrogen or an aliphatic hydrocarbon radical having from 1 to 4 carbon atoms. Examples of suitable aldehydes include formaldehyde, paraformaldehyde, acetaldehyde and the like.

The Mannich bases of this invention were prepared by one of the following general procedures. Procedure A:

A sample of N-(hydroxyphenyl)polyisobutenyl succinimide, an amine, paraformaldehyde, a solvent (if used), a quantity of mineral oil equal in mass to the amount of N-(hydroxyphenyl)polyisobutenyl succinimide plus the amount of amine used, were combined and stirred at the indicated temperature for the specified period of time. The mixture was then stripped of volatile materials to 100°-120° C. (1 mm) and filtered through celite to yield a 50% oil concentrate of the product. Procedure B:

A sample of N-(hydroxyphenyl)polyisobutenyl succinimide, an amine and 37% aqueous formaldehyde were combined and stirred at the indicated temperature for the specified period of time. A quantity of mineral oil, equal in mass to the amount of N-(hydroxyphenyl)-polyisobutenyl succinimide, plus the amount of amine used, was then added to the reaction. The mixture was stripped of volatile materials to 100°-120° C. (20 mm) and filtered through celite to yield a 50% oil concentrate of the product.

The lubricant composition of the invention comprises a major amount of a mineral, hydrocarbon oil or synthetic oil of lubricating viscosity and an effective detergent-dispersant amount of the prescribed Mannich base derivative. Advantageously, in the finished lubricating oil composition, the prescribed Mannich base derivative content ranges between about 0.1 and 10 percent by weight, preferably between about 0.5 and 7 weight percent. In the lubricating oil concentrates, from which the finished lubricating compositions are derived via the addition of added lubricating oil, Mannich base derivative contents between about 10 and 80 weight percent are found.

The hydrocarbon oil in the finished lubricating composition advantageously constitutes at least about 85 weight percent and preferably between about 90 and 98 weight percent of the composition, and in the lube oil concentrates between about 20 and 90 weight percent of the composition. It is to be noted that even in the lubricating oil concentrates the prescribed Mannich base derivatives will exhibit detergent-dispersancy as well as varnish inhibition.

Examples of the hydrocarbon base oils contemplated herein are the naphthenic base, paraffinic base and mixed base mineral oils, lubricating oil derived from coal products and synthetic oils, e.g., alkylene polymers such as polypropylene and polyisobutylene of a molecular weight of between about 250 and 2500. Advantageously, a lubricating base oil having a lubricating oil viscosity at 100° F. of between about 50 and 1000, preferably between about 100 and 600, are normally employed for the lubricant compositions and concentrates thereof (SUS basis).

In the contemplated finished lubricating oil compositions other additives may be included in addition to the dispersant of the invention. The additives may be any of the suitable standard pour depressants, viscosity index improvers, oxidation and corrosion inhibitors, anti-foamants, supplementary detergent-dispersants, etc. The choice of the particular additional additives to be included in the finished oils and the particular amounts thereof will depend on the use and conditions desired for the finished oil product.

Specific examples of the supplementary additives are as follows:

A widely used and suitable VI improver is the polymethacrylate having the general formula:

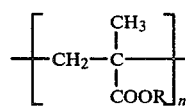

where R is an aliphatic radical of from 1 to 20 carbons and n is an integer of between about 600 and 35,000. One of the most suitable VI improvers is the tetrapolymer of butyl methacrylate, dodecyl methacrylate, octadecyl methacrylate, and dimethylaminoethyl methacrylate having a respective component weight ratio in the polymer of about 4:10:5:1. Another VI improver is a copolymer of ethylene and propylene having a molecular weight of 20,000 to 50,000 containing 30 to 40 percent propylene in the copolymer in admixture with solvent neutral oil (100 E Pale Oil) comprising 13 weight percent copolymer and 87 weight percent oil. The VI improvers are normally employed in the finished lubricant compositions in quantities between about 0.1 and 10 percent by weight.

One of the commonly employed lube oil corrosion inhibitors and antioxidants are the divalent dialkyl dithiophosphates resulting from the neutralization of a $P_2S_5$-alcohol reaction product with a divalent metal or divalent metal oxide. Barium and zinc dialkyl dithiophosphate are specific examples. Another class of antioxidants are the polyalkylated diphenylamines, such as a mixture of 2,2'-diethyl-4,4'-dioctyl-diphenylamine and 2,2'-diethyl-4-octyldiphenylamine. The corrosion and oxidation inhibitors are usually present in the finished lubricating oil compositions in concentrations of between about 0.1 and 3 weight percent.

Examples of supplementary detergent-dispersants which can be employed are the monoethoxylated inorganic phosphorus acid-free, steam hydrolyzed polyalkylene (500-50,000 M.W.)-$P_2S_5$ reaction product, alkaline earth metal alkylphenolates, such as barium nonylphenolate, barium dodecylcresolate, calcium dodecylphenolate and the calcium carbonate overbased calcium alkaryl sulfonates formed by blowing a mixture of calcium hydroxide and calcium alkaryl sulfonate, e.g., calcium alkylbenzene sulfonate of about 900 M.W. with carbon dioxide to form a product having a total base number (TBN) of 50 or more, e.g., 300 to 400.

If antifoamants are employed in the finished compositions, one widely used class which is suitable are the dimethyl silicone polymers employed in amounts of between about 10 and 1000 ppm.

The following tests were employed to determine the dispersancy, varnish inhibiting, and oxidation inhibiting effects of the lubricant oil compositions of this invention.

BENCH VC TEST

In the Bench VC Test, a mixture containing the test oil and the diluent are heated at an elevated temperature. After heating, the turbidity of the resultant mixture is measured. A low % turbidity (0-10) is indicative of good dispersancy while high results (20-100) are indicative of oils of increasingly poor dispersancy.

BENCH IIID TEST

In the Bench IIID Test, a sample of the test oil is subjected to high temperature, oxidizing conditions for 72 hr. An aliquot is removed every 24 hrs and the viscosity recorded in cSt at 100° C. A low % viscosity increase (<250%) is indicative of a well oxidation inhibited oil while high results (>500%) are indicative of oils of poor oxidation stability.

FORD SEQUENCE VD TEST

This test is the Ford Sequence VD Test and is detailed in "Tentative Sequence VD Test Procedure" issued by the ASTM PV-1 Task Force on Nov. 30, 1978. This procedure is used to elevate crankcase motor oils with respect to sludge and varnish deposits. Ratings of 0 to 10 are given, 10 representing absolutely clean and 0 representing heavy sludge and varnish deposits. SE performance criteria for the test specify a 9.2 (min.) for average sludge, 6.3 (min.) for average varnish and 6.4 (min.) for piston skirt varnish.

EXAMPLE 24

A fully formulated SAE Grade 10W-40 lubricating oil composition containing the Mannich base of the invention was tested for its dispersing effectiveness in the Bench VC Test in comparison to a fully formulated base oil without the Mannich Base dispersant, and to fully formulated lubricating oil compositions containing either a commercial succinimide dispersant or the intermediate N-(hydroxyphenyl) polyisobutenyl succinimide.

The base blend employed contained the following conventional additives:
0.15% zinc as zinc dialkyldithiophosphate
0.23% calcium as overbased calcium sulfonate
0.25 weight % alkylated diphenylamine antioxidant
11.5 weight % ethylene-propylene copolymer VI improver
0.15 weight % ethoxylated alkylphenol
0.10 weight % methacrylate pour depressant
150 ppm silicone antifoamant
mineral oil-balance The Mannich base dispersant of the invention was added to the base blend at several concentrations on an oil-free basis and then tested in the Bench VC Test.

The results are set forth in Table II.

TABLE II

| | Bench VC Test Data | | |
| Run | | Wt. % of Additive in Base Blend | Turbidity |
| --- | --- | --- | --- |
| 1 | Base Blend | (no dispersant) | 97.5 |
| 2 | Example 5 | 4.0 | 4.0 |
| 3 | Example 5 | 3.0 | 4.5 |
| 4 | Example 6 | 4.0 | 4.0 |
| 5 | Example 6 | 3.0 | 4.5 |
| 6 | Example 7 | 4.0 | 2.5 |
| 7 | Example 7 | 3.0 | 3.5 |

TABLE II-continued

Bench VC Test Data

| Run | | Wt. % of Additive in Base Blend | Turbidity |
|---|---|---|---|
| 8 | Example 8 | 3.0 | 7.0 |
| 9 | Example 9 | 4.0 | 4.0 |
| 10 | Example 9 | 3.0 | 3.5 |
| 11 | Example 10 | 4.0 | 5.5 |
| 12 | Example 10 | 3.0 | 8.0 |
| 13 | Example 11 | 4.0 | 3.0 |
| 14 | Example 11 | 3.0 | 5.0 |
| 15 | Example 12 | 4.0 | 3.5 |
| 16 | Example 12 | 3.0 | 3.0 |
| 17 | Example 13 | 4.0 | 3.5 |
| 18 | Example 13 | 3.0 | 2.5 |
| 19 | Example 14 | 3.0 | 4.0 |
| 20 | Example 15 | 4.0 | 3.0 |
| 21 | Example 15 | 3.0 | 4.0 |
| 22 | Example 16 | 4.0 | 4.5 |
| 23 | Example 17 | 4.0 | 8.0 |
| 24 | Example 18 | 4.0 | 5.0 |
| 25 | Example 19 | 4.0 | 3.5 |
| 26 | Example 19 | 3.0 | 3.5 |
| 27 | Example 20 | 4.0 | 2.0 |
| 28 | Example 20 | 3.0 | 3.0 |
| 29 | Example 21 | 4.0 | 4.0 |
| 30 | Example 21 | 3.0 | 6.0 |
| 31 | Example 22 | 4.0 | 5.5 |
| 32 | Example 22 | 3.0 | 4.5 |
| 33 | Example 23 | 4.0 | 4.0 |
| 34 | Example 23 | 3.0 | 5.0 |
| 35 | Example 1 | 4.0 | 87.5 |
| 36 | Example 1 | 3.0 | 90.0 |
| 37 | Succinimide Dispersant | 4.0 | 4.0 |
| 38 | Succinimide Dispersant | 3.0 | 8.5 |

EXAMPLE 25

A fully formulated SAE Grade 30 lubricating oil composition containing the Mannich base of the invention was tested for its effectiveness as an oxidation inhibitor in the Bench IIID Test in comparison to a fully formulated oil containing a commercial succinimide dispersant.

The base blend employed contained the following conventional additives:
0.12% zinc as zinc dialkyldithiophosphate
0.23% calcium as overbased calcium sulfonate
0.10 weight % dinonyldiphenylamine
0.15 weight % ethoxylated alkyphenol
0.05 weight % methacrylate pour depressant
150 ppm silicone antifoamant
mineral oil—balance The dispersants tested were added to the base blend at 8.00 weight % as a 50% oil concentrate and evaluated in the Bench IIID Test.

The results are set forth in Table III.

TABLE III

| Dispersant Type | Bench IIID % Viscosity Increase | | |
|---|---|---|---|
| 8.0 wt. % | 24 hrs. | 48 hrs. | 72 hrs |
| Mannich Base (Example 5) | 16.3 | 37.7 | 219 |
| Mannich Base (Example 6) | 14.5 | 60.7 | 194 |
| Mannich Base (Example 6) | 13.7 | 51.7 | 184 |
| Mannich Base (Example 7) | 17.9 | 47.6 | 125 |
| Mannich Base (Example 13) | 12.5 | 58.5 | 155 |
| Mannich Base (Example 15) | 6.8 | 31.5 | 183 |
| Commercial Succinimide | 16.8 | 70.4 | TVTM* |
| Commercial Succinimide | 28.8 | 182.0 | TVTM* |

*TVTM = Too viscous to measure.

The foregoing tests demonstrate that the prescribed Mannich bases are excellent dispersants and antioxidants for a lubricating oil composition and exhibit superior effectiveness in comparison to a commercial succinimide dispersant.

EXAMPLE 26

This example illustrates the dispersant properties of the lubricating oil compositions of the invention in the Ford Sequence VD Test described above. The blend employed in this test was formulated SAE Grade 30 mineral lubricating oil composition. The composition of the lubricant and the test results are set forth in the Table below:

TABLE

| Composition | Wt. % |
|---|---|
| Dispersant of Example 5 | 6.20 |
| 0.15% zinc as zinc dialkyldithiophosphate | 1.31 |
| 0.23% calcium as overbased calcium sulfonate | 1.64 |
| Dinonyldiphenylamine | 0.25 |
| Methacrylate pour depressant | 0.05 |
| Ethoxylated alkylphenol | 0.15 |
| Silicone antifoamant | 150 ppm |
| Mineral oil | balance |
| SEQUENCE VD TEST RESULTS | |
| Sludge (Average) | 9.44 |
| Varnish (Average) | 7.14 |
| Piston Skirt Varnish | 7.52 |

EXAMPLE 27

This example further illustrates the dispersant properties of the lubricating oil compositions of the invention in the Ford Sequence VD Test. The blend employed in this test was a formulated SAE Grade 10W-40 mineral lubricating oil composition. The composition of the lubricant and the test results are set forth in the table below:

TABLE

| Composition | Wt. % |
|---|---|
| Dispersant of Example 6 | 7.50 |
| 0.15% zinc as zinc dialkyldithiophosphate | 1.05 |
| 0.23% calcium as overbased calcium sulfonate | 1.64 |
| Dinonyldiphenyl amine | 0.25 |
| Alkylated phenol | 0.25 |
| Methacrylate pour depressant | 0.10 |
| Ethylene-propylene copolymer VII | 11.50 |
| Ethoxylated Alkylphenol | 0.15 |
| Friction Modifier | 1.00 |
| Silicone Antifoamant | 150 ppm |
| Mineral Oil | balance |
| SEQUENCE VD TEST RESULTS | |
| Sludge (Average) | 9.3 |
| Varnish (Average) | 8.1 |
| Piston Skirt Varnish | 8.0 |

The foregoing two examples indicate outstanding engine cleanliness for the lubricating oil composition of the invention in the Ford Sequence VD Engine Test.

We claim:

1. A Mannich base derivative of a hydroxyaryl succinimide represented by the formula:

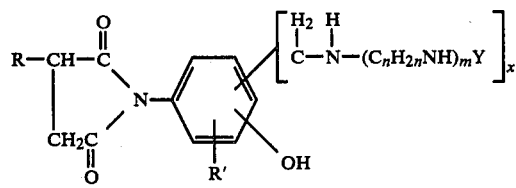

in which R is a hydrocarbyl radical having from about 25 to 200 carbon atoms, R' is hydrogen, an alkyl radical or a halogen radical, n has a value of 2 or 3, m has a value from 1 to 5, Y is hydrogen or a methylene hydroxyaryl succinimide radical, and x has a value of 1 to 2 when Y is hydrogen and a value of 1 when Y is a methylene hydroxyaryl succinimide radical.

2. A Mannich base derivative of a hydroxyaryl succinimide represented by the formula:

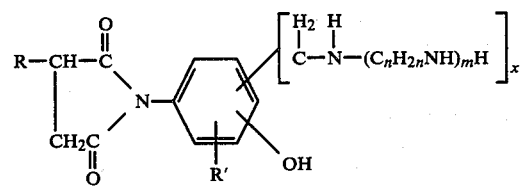

in which R is a hydrocarbyl radical having from about 25 to 200 carbon atoms, R' is hydrogen, an alkyl radical or a halogen radical, n has a value of 2 or 3, m has a value from 1 to 5, and x has a value from 1 to 2.

3. A Mannich base derivative of a hydroxyaryl succinimide represented by the formula:

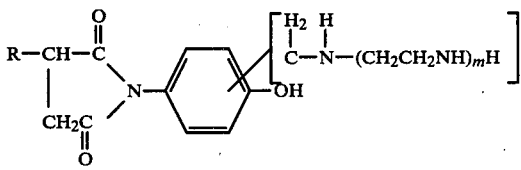

in which R is a hydrocarbyl radical having from about 50 to 100 carbon atoms, m has a value from 1 to 3, and x has a value from 1 to 2.

4. A Mannich base derivative according to claim 1 in which said methylene hydroxyaryl succinimide radical has the formula:

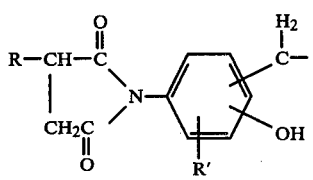

5. A compound according to claim 1 in which R represents an alkenyl radical.

6. A compound according to claim 1 in which R represents a polyisobutenyl radical.

7. A lubricating oil composition comprising a major portion of a mineral lubricating oil and a minor dispersant amount of a Mannich base derivative of a hydroxyaryl succinimide represented by the formula:

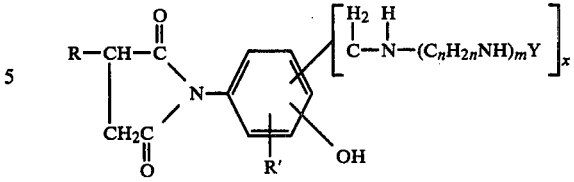

in which R is a hydrocarbyl radical having from about 25 to 200 carbon atoms, R' is hydrogen, an alkyl radical or a halogen radical, n has a value of 2 or 3, m has a value from 1 to 5, Y is hydrogen or a methylene hydroxyaryl succinimide radical, and x has a value of 1 to 2 when Y is hydrogen and a value of 1 when Y is a methylene hydroxyaryl succinimide radical.

8. A lubricating oil composition comprising a major portion of a mineral lubricating oil and a minor dispersant amount of a Mannich base derivative of a hydroxyaryl succinimide represented by the formula:

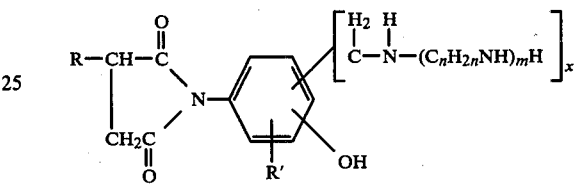

in which R is a hydrocarbyl radical having from about 25 to 200 carbon atoms, R' is hydrogen, an alkyl radical or a halogen radical, n has a value of 2 or 3, m has a value from 1 to 5, and x has a value from 1 to 2.

9. A lubricating oil compositon according to claim 7 in which said methylene hydroxyaryl succinimide radical has the formula:

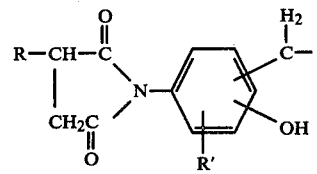

10. A lubricating oil composition comprising a major portion of a mineral lubricating oil and a minor dispersant amount of a Mannich base derivative of a hydroxyaryl succinimide represented by the formula:

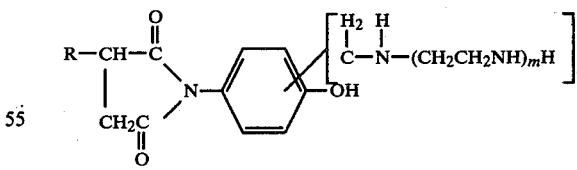

in which R is a hydrocarbyl radical having from about 50 to 100 carbon atoms, m has a value from 1 to 3 and x has a value from 1 to 2.

11. A lubricating oil composition according to claim 7 in which R represents an alkenyl radical.

12. A lubricating oil composition according to claim 7 in which R represents a polyisobutenyl radical.

13. A lubricating oil composition according to claim 7 containing from about 0.1 to 10 weight percent of said Mannich base derivative of a hydroxyaryl succinimide.

* * * * *